(12) United States Patent
Shea et al.

(10) Patent No.: US 9,002,468 B2
(45) Date of Patent: Apr. 7, 2015

(54) AUTOMATIC POWER REGULATION FOR TRANSCUTANEOUS ENERGY TRANSFER CHARGING SYSTEM

(75) Inventors: Arthur Shea, Beverly, MA (US); Ralph D. Ambrosio, Wenham, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 13/328,568

(22) Filed: Dec. 16, 2011

(65) Prior Publication Data
US 2013/0158631 A1    Jun. 20, 2013

(51) Int. Cl.
*A61N 1/05* (2006.01)
*A61N 1/378* (2006.01)
*A61N 1/08* (2006.01)

(52) U.S. Cl.
CPC ............... *A61N 1/3787* (2013.01); *A61N 1/08* (2013.01)

(58) Field of Classification Search
None
See application file for complete search history.

(56) References Cited

U.S. PATENT DOCUMENTS

| | | | |
|---|---|---|---|
| 3,195,038 A | 7/1965 | Fry | |
| 3,195,540 A | 7/1965 | Waller | |
| 3,357,432 A | 12/1967 | Sparks | |
| 3,357,434 A | 12/1967 | Abell | |
| 3,711,747 A | 1/1973 | Sahara et al. | |
| 3,756,246 A | 9/1973 | Thaler et al. | |
| 3,824,129 A | 7/1974 | Fagan, Jr. | |
| 3,825,925 A | 7/1974 | Drusch | |
| 3,866,616 A | 2/1975 | Purdy et al. | |
| 3,867,950 A | 2/1975 | Fischell | |
| 3,888,260 A | 6/1975 | Fischell | |
| 3,915,038 A | 10/1975 | Malin | |
| 3,934,177 A | 1/1976 | Horbach | |
| 3,942,535 A | 3/1976 | Schulman | |
| 3,987,799 A | 10/1976 | Purdy et al. | |
| 3,995,137 A | 11/1976 | Okada et al. | |
| 4,011,499 A | 3/1977 | Betsill et al. | |

(Continued)

FOREIGN PATENT DOCUMENTS

| | | |
|---|---|---|
| DE | 2720011 A1 | 11/1978 |
| EP | 0 507 360 A2 | 10/1992 |

(Continued)

OTHER PUBLICATIONS

[No Author Listed] SBS 1.1-Compliant Gas Gauge and Protection Enabled with Impedance Track™, Texas Instruments, SLUS757B—Jul. 2007, Revised Apr. 2008. 18 pages.

(Continued)

*Primary Examiner* — Brian T Gedeon
*Assistant Examiner* — Ankit Tejani
(74) *Attorney, Agent, or Firm* — Thomas J. Engellenner; Reza Mollaaghababa; Pepper Hamilton LLP

(57) ABSTRACT

Methods and systems for controlling power output from an external power source in a transcutaneous energy transfer (TET) system are provided to prevent inadvertent energy transfer when no secondary coil is present. The system operates by transmitting power transcutaneously from an external primary coil and determining whether a response from a secondary coil implanted within a patient is detected. If no response is detected, the power output of the primary coil is decreased. The decrease in power output can be accomplished by operating the primary coil at a lower average power level, which can include variations in power level, duty cycle, etc. The system can also be configured to periodically repeat the process in order to continue searching for a coupled secondary coil.

20 Claims, 6 Drawing Sheets

(56) References Cited

U.S. PATENT DOCUMENTS

| | | |
|---|---|---|
| 4,012,769 A | 3/1977 | Edwards et al. |
| 4,041,955 A | 8/1977 | Kelly et al. |
| 4,068,292 A | 1/1978 | Berry et al. |
| 4,071,032 A | 1/1978 | Schulman |
| 4,104,701 A | 8/1978 | Baranowski |
| 4,134,408 A | 1/1979 | Brownlee et al. |
| 4,143,661 A | 3/1979 | LaForge et al. |
| 4,186,749 A | 2/1980 | Fryer |
| 4,266,533 A | 5/1981 | Ryaby et al. |
| 4,441,210 A | 4/1984 | Hochmair et al. |
| 4,441,498 A | 4/1984 | Nordling |
| 4,517,585 A | 5/1985 | Ridout et al. |
| 4,539,433 A | 9/1985 | Ishino et al. |
| 4,586,508 A | 5/1986 | Batina et al. |
| 4,665,896 A | 5/1987 | LaForge et al. |
| 4,673,888 A | 6/1987 | Engelmann et al. |
| 4,678,986 A | 7/1987 | Barthelemy |
| 4,679,560 A | 7/1987 | Galbraith |
| 4,716,353 A | 12/1987 | Engelmann |
| 4,717,889 A | 1/1988 | Engelmann |
| 4,741,339 A | 5/1988 | Harrison et al. |
| 4,808,924 A | 2/1989 | Cecco et al. |
| 4,837,497 A | 6/1989 | Leibovich |
| 4,924,171 A | 5/1990 | Baba et al. |
| 4,925,443 A | 5/1990 | Heilman et al. |
| 4,944,299 A | 7/1990 | Silvian |
| 5,000,178 A | 3/1991 | Griffith |
| 5,004,489 A | 4/1991 | Rotman et al. |
| 5,109,843 A | 5/1992 | Melvin et al. |
| 5,214,392 A | 5/1993 | Kobayashi et al. |
| 5,312,439 A | 5/1994 | Loeb |
| 5,314,453 A | 5/1994 | Jeutter |
| 5,324,316 A | 6/1994 | Schulman et al. |
| 5,350,411 A | 9/1994 | Ryan et al. |
| 5,350,413 A | 9/1994 | Miller et al. |
| 5,355,296 A | 10/1994 | Kuo et al. |
| 5,358,514 A | 10/1994 | Schulman et al. |
| 5,383,912 A | 1/1995 | Cox et al. |
| 5,411,536 A | 5/1995 | Armstrong |
| 5,411,537 A | 5/1995 | Munshi et al. |
| 5,480,415 A | 1/1996 | Cox et al. |
| 5,506,503 A | 4/1996 | Cecco et al. |
| 5,527,348 A | 6/1996 | Winkler et al. |
| 5,545,191 A | 8/1996 | Mann et al. |
| 5,556,421 A | 9/1996 | Prutchi et al. |
| 5,569,156 A | 10/1996 | Mussivand |
| 5,613,935 A | 3/1997 | Jarvik |
| 5,621,369 A | 4/1997 | Gardner et al. |
| 5,630,836 A | 5/1997 | Prem et al. |
| 5,690,693 A | 11/1997 | Wang et al. |
| 5,702,431 A | 12/1997 | Wang et al. |
| 5,713,939 A | 2/1998 | Nedungadi et al. |
| 5,722,998 A | 3/1998 | Prutchi et al. |
| 5,730,125 A | 3/1998 | Prutchi et al. |
| 5,733,313 A | 3/1998 | Barreras, Sr. et al. |
| 5,735,887 A | 4/1998 | Barreras, Sr. et al. |
| 5,740,257 A | 4/1998 | Marcus |
| 5,741,316 A | 4/1998 | Chen et al. |
| 5,749,909 A | 5/1998 | Schroeppel et al. |
| 5,755,748 A | 5/1998 | Borza et al. |
| 5,861,019 A | 1/1999 | Sun et al. |
| 5,948,006 A | 9/1999 | Mann |
| 5,951,459 A | 9/1999 | Blackwell |
| 5,959,522 A | 9/1999 | Andrews |
| 5,963,132 A | 10/1999 | Yoakum |
| 5,978,713 A | 11/1999 | Prutchi et al. |
| 5,991,665 A | 11/1999 | Wang et al. |
| 5,995,874 A | 11/1999 | Borza et al. |
| 6,047,214 A | 4/2000 | Mueller et al. |
| 6,048,601 A | 4/2000 | Yahagi et al. |
| 6,058,330 A | 5/2000 | Borza et al. |
| 6,067,474 A | 5/2000 | Schulman et al. |
| 6,141,592 A | 10/2000 | Pauly |
| 6,144,841 A * | 11/2000 | Feeney ............ 455/69 |
| 6,149,683 A | 11/2000 | Lancisi et al. |
| 6,212,430 B1 | 4/2001 | Kung |
| 6,243,608 B1 | 6/2001 | Pauly et al. |
| 6,275,737 B1 | 8/2001 | Mann |
| 6,278,258 B1 | 8/2001 | Echarri et al. |
| 6,321,118 B1 | 11/2001 | Hahn |
| 6,324,430 B1 | 11/2001 | Zarinetchi et al. |
| 6,324,431 B1 | 11/2001 | Zarinetchi et al. |
| 6,327,504 B1 | 12/2001 | Dolgin et al. |
| 6,349,234 B2 | 2/2002 | Pauly et al. |
| 6,366,817 B1 | 4/2002 | Kung |
| 6,389,318 B1 | 5/2002 | Zarinetchi et al. |
| 6,395,027 B1 | 5/2002 | Snyder |
| 6,400,991 B1 | 6/2002 | Kung |
| 6,415,186 B1 | 7/2002 | Chim et al. |
| 6,430,444 B1 | 8/2002 | Borza et al. |
| 6,442,434 B1 | 8/2002 | Zarinetchi et al. |
| 6,443,891 B1 | 9/2002 | Grevious |
| 6,445,956 B1 | 9/2002 | Laird et al. |
| 6,478,820 B1 | 11/2002 | Weiss |
| 6,496,733 B2 | 12/2002 | Zarinetchi et al. |
| 6,507,759 B1 | 1/2003 | Prutchi et al. |
| 6,542,777 B1 | 4/2003 | Griffith et al. |
| 6,553,263 B1 | 4/2003 | Meadows et al. |
| 6,591,139 B2 | 7/2003 | Loftin et al. |
| 6,631,296 B1 | 10/2003 | Parramon et al. |
| 6,745,077 B1 | 6/2004 | Griffith et al. |
| 6,748,273 B1 | 6/2004 | Obel et al. |
| 6,772,011 B2 | 8/2004 | Dolgin |
| 6,959,213 B2 | 10/2005 | Prutchi et al. |
| 6,959,217 B2 | 10/2005 | DelMain et al. |
| 6,968,234 B2 | 11/2005 | Stokes |
| 7,015,769 B2 | 3/2006 | Schulman et al. |
| 7,027,871 B2 | 4/2006 | Burnes et al. |
| 7,062,331 B2 | 6/2006 | Zarinetchi et al. |
| 7,076,304 B2 | 7/2006 | Thompson |
| 7,079,901 B1 | 7/2006 | Loftin et al. |
| 7,092,762 B1 | 8/2006 | Loftin et al. |
| 7,151,914 B2 | 12/2006 | Brewer |
| 7,155,291 B2 | 12/2006 | Zarinetchi et al. |
| 7,177,690 B2 | 2/2007 | Woods et al. |
| 7,184,836 B1 | 2/2007 | Meadows et al. |
| 7,191,007 B2 | 3/2007 | Desai et al. |
| 7,225,032 B2 | 5/2007 | Schmeling et al. |
| 7,237,712 B2 | 7/2007 | DeRocco et al. |
| 7,248,929 B2 | 7/2007 | Meadows et al. |
| 7,286,880 B2 | 10/2007 | Olson et al. |
| 7,286,881 B2 | 10/2007 | Schommer et al. |
| 7,295,878 B1 | 11/2007 | Meadows et al. |
| 7,308,316 B2 | 12/2007 | Schommer |
| 7,418,297 B2 | 8/2008 | Bornhoft et al. |
| 7,437,644 B2 | 10/2008 | Ginggen et al. |
| 7,471,986 B2 | 12/2008 | Hatlestad |
| 7,482,783 B2 | 1/2009 | Schommer |
| 7,512,443 B2 | 3/2009 | Phillips et al. |
| 7,515,012 B2 | 4/2009 | Schulman et al. |
| 7,515,967 B2 | 4/2009 | Phillips et al. |
| 7,532,932 B2 | 5/2009 | Denker et al. |
| 7,599,743 B2 | 10/2009 | Hassler, Jr. et al. |
| 7,599,744 B2 | 10/2009 | Giordano et al. |
| 7,632,235 B1 * | 12/2009 | Karicherla et al. ............ 600/526 |
| 7,658,196 B2 | 2/2010 | Ferreri et al. |
| 7,689,176 B2 | 3/2010 | Crivelli |
| 7,711,435 B2 | 5/2010 | Schommer |
| 7,738,965 B2 | 6/2010 | Phillips et al. |
| 7,751,899 B1 | 7/2010 | Karunasiri |
| 7,751,902 B1 | 7/2010 | Karunasiri |
| 7,775,444 B2 | 8/2010 | DeRocco et al. |
| 7,813,801 B2 | 10/2010 | Youker et al. |
| 7,818,068 B2 | 10/2010 | Meadows et al. |
| 7,822,480 B2 | 10/2010 | Park et al. |
| 7,848,814 B2 | 12/2010 | Torgerson et al. |
| 7,856,986 B2 | 12/2010 | Darley |
| 2002/0016568 A1 | 2/2002 | Lebel et al. |
| 2003/0065366 A1 | 4/2003 | Merritt et al. |
| 2003/0088295 A1 | 5/2003 | Cox |
| 2003/0163020 A1 | 8/2003 | Frazier |
| 2003/0171792 A1 | 9/2003 | Zarinetchi et al. |
| 2004/0039423 A1* | 2/2004 | Dolgin ............ 607/27 |
| 2005/0075693 A1 | 4/2005 | Toy et al. |

(56) References Cited

U.S. PATENT DOCUMENTS

| | | |
|---|---|---|
| 2005/0075696 A1 | 4/2005 | Forsberg et al. |
| 2005/0107847 A1 | 5/2005 | Gruber et al. |
| 2005/0113887 A1 | 5/2005 | Bauhahn et al. |
| 2005/0288739 A1 | 12/2005 | Hassler et al. |
| 2005/0288740 A1 | 12/2005 | Hassler et al. |
| 2005/0288743 A1 | 12/2005 | Ahn et al. |
| 2006/0020300 A1 | 1/2006 | Nghiem et al. |
| 2006/0020305 A1 | 1/2006 | Desai et al. |
| 2006/0107148 A1 | 5/2006 | Ginggen et al. |
| 2006/0197494 A1 | 9/2006 | Schommer |
| 2006/0247737 A1 | 11/2006 | Olson et al. |
| 2007/0049983 A1 | 3/2007 | Freeberg |
| 2007/0106274 A1 | 5/2007 | Ayre et al. |
| 2007/0142696 A1 | 6/2007 | Crosby et al. |
| 2007/0255349 A1 | 11/2007 | Torgerson et al. |
| 2007/0270921 A1 | 11/2007 | Strother et al. |
| 2008/0027500 A1 | 1/2008 | Chen |
| 2008/0027513 A1 | 1/2008 | Carbunaru |
| 2008/0065290 A1* | 3/2008 | Breed et al. ............... 701/29 |
| 2008/0129517 A1 | 6/2008 | Crosby et al. |
| 2008/0167531 A1 | 7/2008 | McDermott |
| 2008/0312852 A1 | 12/2008 | Maack |
| 2009/0069869 A1 | 3/2009 | Stouffer et al. |
| 2009/0112291 A1* | 4/2009 | Wahlstrand et al. ............ 607/61 |
| 2009/0157148 A1 | 6/2009 | Phillips et al. |
| 2009/0273349 A1 | 11/2009 | Rondoni et al. |
| 2009/0276016 A1 | 11/2009 | Phillips et al. |
| 2010/0063347 A1* | 3/2010 | Yomtov et al. ................ 600/17 |
| 2010/0076524 A1 | 3/2010 | Forsberg et al. |
| 2010/0080025 A1* | 4/2010 | Terlizzi et al. ................. 363/78 |
| 2010/0222848 A1 | 9/2010 | Forsell |
| 2010/0305662 A1 | 12/2010 | Ozawa et al. |
| 2010/0312188 A1* | 12/2010 | Robertson et al. ............ 604/156 |
| 2011/0009924 A1 | 1/2011 | Meskens |
| 2011/0101790 A1 | 5/2011 | Budgett |
| 2011/0160516 A1 | 6/2011 | Dague et al. |
| 2011/0193688 A1* | 8/2011 | Forsell ........................ 340/10.4 |
| 2011/0196452 A1 | 8/2011 | Forsell |
| 2011/0278948 A1 | 11/2011 | Forsell |
| 2012/0154143 A1 | 6/2012 | D'Ambrosio |
| 2012/0157753 A1 | 6/2012 | D'Ambrosio |
| 2012/0157754 A1 | 6/2012 | D'Ambrosio |
| 2012/0157755 A1 | 6/2012 | D'Ambrosio |
| 2012/0265003 A1 | 10/2012 | D'Ambrosio et al. |

FOREIGN PATENT DOCUMENTS

| | | |
|---|---|---|
| JP | 07-046164 A | 2/1995 |
| JP | H10215530 A | 8/1998 |
| JP | H10258129 A | 9/1998 |
| JP | 2002034169 A | 1/2002 |
| JP | 2010-284065 A | 12/2010 |
| JP | 2010284065 A | 12/2010 |
| WO | 97/29802 A2 | 8/1997 |
| WO | 97/47065 A1 | 12/1997 |
| WO | 99/44684 A1 | 9/1999 |
| WO | 2006096685 A1 | 9/2006 |
| WO | 2008/106717 A1 | 9/2008 |
| WO | 2011008163 A1 | 1/2011 |

OTHER PUBLICATIONS

[No Author Listed] Low-power SoC (system-on-chip) with MCU, memory sub-1 ghz RF transceiver, and USB controller. TIRF Common Spec (CC1110Fx/CC1111Fx), Texas Instruments, Jul. 20, 2010, 247 pages.

[No Author Listed] Battery Spec NCR 18650. NNP Series. Panasonic. Feb. 2010, 1 page.

Abe et al., Development of transcutaneous energy transmission system for totally implantable artificial heart. Artificial Heart 2/Proceedings of the 2nd International Symposium on Artificial Heart and Assist Device. Akutsu, T. ed, Springer-Verlag, Tokyo, pp. 257-261, 1988.

Ahn et al., In Vivo Performance Evaluation of a Transcutaneous Energy and Information Transmission System for the Total Artificial Heart, ASAIO Journal 1993, M208-M212.

Barsukov, Theory and Implementation of Impedance Track™ Battery Fuel-Gauging Algorithm in bq20z8x Product Family, Texas Instruments, SLUA364, Nov. 2005. 8 pages.

Bearnson et al., Electronics Development for the Utah Electrohydrolic Total Artificial Heart. Sixth Annual IEEE Symposium on Computer-Based Medical Systems, 247-252 (1993).

Callewaert et al., A Programmable Implantable Stimulator with Percutaneous Optical Control. Ninth Annual Conference of the Engineering in Medicine and Biology Society IEEE, 1370-1371 (1987).

Davies et al., Adaptation of Tissue to a Chronic Heat Load, ASAIO Journal. 40(3), M514-7 (1994).

Donaldson, Nde N, Use of feedback with voltage regulators for implants powered by coupled coils. Med Biol Eng Comput. May 1985;23(3):291, XP002066875, ISSN: 0140-0118.

Fraim et al. Performance of a tuned ferrite core transcutaneous transformer. IEEE Trans Bio-med Eng. Sep. 1971;BME-18(5):352-9.

Galbraith et al, A Wide-Band Efficient Inductive Transdermal Power and Data Link with Coupling Insensitive Gain. IEEE Transactions on Biomedical Engineering, BME 34(4):265-275 (1987).

Geselowitz et al., The effects of metals on a transcutaneous energy transmission system. IEEE Transactions on Biomedical Engineering. vol. 39(9), pp. 928-934, Sep. 1992.

International Search Report and Written Opinion for Application No. PCT/US2011/065487, mailed Aug. 30, 2012. (9 pages).

Masuzawa, T., et al., Set-up, Improvement, and Evaluation of an Electrohydraulic Total Artificial Heart with a Separately Placed Energy Converter. (1996) ASAIO Journal, vol. 42; M328-M332.

Matsuki et al. Energy Transferring System Reducing Temperature Rise for Implantable Power Consuming Devices. Proceedings of the 18th Annual Conference of the IEEE Engineering in Medicine and Biology Society, Amsterdam Oct. 31-Nov. 3, 1996, vol. 1, pp. 185-186.

Matsuki et al., Signal Transmission for Implantable Medical Devices using Figure-of-eight Coils, IEEE Transactions on Magnetics, vol. 32 No. 5, pp. 5121-5123, Sep. 1996.

Melvin, D.B., et al., Electric Power Induction Through an Isolated Intestinal Pouch. (1991) Trans. Am. Soc. Intern. Organs, vol. XXXVII;M203-M204.

Miller et al. Development of an Autotuned Transcutaneous Energy Transfer System. ASAIO Journal. 1993;39:M706-M710.

Mitamura et al. Development of an Implantable Motor-Driven Assist Pump System. IEEE Transactions on Biomedical Engineering. vol. 37(2), pp. 146-156, 1990.

Mitamura et al. A Transcutaneous Optical Information Transmission System for Implantable Motor-drive Artificial Hearts. ASAIO Transactions.1990;36:M278-M280.

Mohammed et al. A miniature DC-DC converter for energy producing implantable devices. IEEE Ninth Annual Conference of the Engineering in Medicine and Biology Society, 1147-1148, 1987.

Mohammed, Design of radio frequency powered coils for implantable stimulators. IEEE Ninth Annual Conference of the Engineering in Medicine and Biology Society, 1378-1379, 1987.

Mussivand et al. Remote energy transmission for powering artificial hearts and assist devices. Artificial Heart 6/6th International Symposium on Artificial Heart and Assist Devices. Akutsu et al., eds., Springer-Verlag, Tokyo, pp. 344-347, 1998.

Mussivand et al. Transcutaneous energy transfer system performance evaluation. Artificial Organs. May 1993;17 (11):940-947.

Myers et al. A transcutaneous power transformer. Transactions of the American Society for Artificial Internal Organs, vol. 14, pp. 210-214, 1968.

Phillips, R.P., A High Capacity Transcutaneous Energy Transmission System. ASAIO Journal, vol. 41: M259-M262 (1995).

Rintoul et al, Continuing Development of the Cleveland Clinic-Nimbus Total Artificial Heart. ASAIO Journal, 39: M168-171 (1993).

Rosenberg et al., Progress Towards a Totally Implantable Artificial Heart. Cardiovascular Science & Technology: Basic & Applied, I. Precised Proceedings, pp. 214-216 (1989-1990).

(56) References Cited

OTHER PUBLICATIONS

Sherman et al., Energy Transmission Across Intact Skin for Powering Artificial Internal Organs. Trans. Am. Soc. Artificial Intern Organs, vol. XXVII, 1981, pp. 137-141.

Sherman et al., Transcutaneous energy transmission (TET) system for energy intensive prosthetic devices. Progress in Artificial Organs. 1985;400-404.

Sutton, A miniaturized device for electrical energy transmission through intact skin-concepts and sesults of initial tests. Third Meeting of the International Society for Artificial Organs. vol. 5, abstracts, Jul. 1981, pp. 437-440.

Weiss et al. A telemetry system for the implanted total artificial heart and ventricular assist device. IEEE Ninth Annual Conference of the Engineering in medicine and Biology Society, pp. 186-187, 1987.

Weiss et al., Permanent Circulatory Support at the Pennsylvania State University. IEEE Transaction on Biomedical Engineering 37(2):138-145 (Feb. 1990).

Extended European Search Report for EP Application No. 11877480.1, mailed May 27, 2014 (9 pages).

English Translation of Notification of Reasons for Refusal for JP 2014-518540, dated Jul. 15, 2014 (11 pages).

* cited by examiner

AUTOMATIC POWER REGULATION FOR TRANSCUTANEOUS ENERGY TRANSFER CHARGING SYSTEM

FIELD

The technical field of this invention is transcutaneous energy transfer (TET) systems and, in particular, methods and systems for regulating energy transfer from an external power source in order to avoid inadvertent power transfer when the external power source is not coupled to an implanted medical device.

BACKGROUND

In a variety of scientific, industrial, and medically related applications, it can be desirable to transfer energy or power across some type of boundary. For example, one or more devices that require power can be located within the confines of a closed system in which it may be difficult and/or undesirable to include a substantial and/or long term source of power. It can also be undesirable to repeatedly enter the closed system for a variety of reasons. In these cases, a power source external to the closed system and some feasible means of transferring power from the external source to one or more internal devices without direct electrical conduction can be preferable.

One example of a closed system is the human body. In several medically related and scientific applications, a variety of prosthetic and other devices that require power may be surgically implanted within various portions of the body. Examples of such devices include a synthetic replacement heart, a circulatory blood pump or ventricular assist device (VAD), and the like. With respect to the human body, complications associated with repeated surgical entry make replaceable internal power sources impractical. Likewise, the risk of infection and/or dislodgment makes direct electrical linkages between external power supplies and implanted devices undesirable.

Accordingly, transcutaneous energy transfer (TET) systems are employed to transfer energy from outside the body to inside the body in order to provide power to one or more implanted devices from an external power source. TET systems use an inductive link to transfer power without puncturing the skin. Thus, the possibility of infection is reduced while comfort and convenience for patients is increased.

TET devices typically include an external primary coil and circuitry, along with an implanted secondary coil and circuitry that are separated by intervening layers of tissue. The primary coil is designed to induce alternating current in the subcutaneously placed secondary coil, typically for transformation to direct current to power an implanted device. TET devices therefore also typically include electrical circuits for periodically providing appropriate alternating current to the primary coil. These circuits typically receive their power from an external power source.

As a result of the power demands of exemplary implanted medical devices, such as a VAD, the TET primary coil must frequently be coupled to the implanted secondary coil to supply power from the external power source. Accordingly, it is desirable for the external power source and primary coil to have a simple, automated operation that can easily be used by a patient, nurse, or doctor. In prior art implementations, this is accomplished via an "always on" configuration, where the primary coil constantly transmits power when connected to an external power source.

However, such prior art implementations can have several drawbacks. For example, if a patient or practitioner decouples the primary coil from the implanted secondary coil for any reason (e.g., to reposition a patient, change clothes, etc.), the primary coil can inadvertently transfer power into surrounding objects. A typical example may be a patient who removes a primary coil from their skin in order to change clothing. The patient may place the primary coil on, for example, a stainless steel table in a hospital. The primary coil, however, may continue to transmit power as if it were coupled to the secondary coil. This continued transfer of power can result in undesirable heating of the metal table or other objects placed on the table.

In addition, the external power source may be a limited capacity source, such as a battery pack. In such a case, the continued transfer of power when the primary coil is decoupled from the secondary coil is extremely inefficient and undesirably depletes the battery pack charge.

Hence, there is a need for a method of controlling power output from a primary coil in a TET system in order to avoid inadvertent transmission of power when the primary coil is not coupled to an implanted secondary coil.

SUMMARY

To overcome the above and other drawbacks of conventional systems, the present invention provides methods and systems for controlling the power output from an external component of a transcutaneous energy transfer (TET) system to avoid undesirable transmission of energy when no internal component is in close proximity. The methods and systems of the present invention allow the external components of a TET system to retain a simple and automated user experience, while preventing the undesirable transmission of power that can result in inadvertent heating of nearby objects and depletion of limited capacity power sources.

In one aspect of the invention, a method of controlling power output from an external, primary coil in a transcutaneous energy transfer system is provided comprising the steps of transcutaneously transmitting power from the primary coil and determining whether a response from a secondary coil within a patient is detected. The method further includes, if no response is received, decreasing the power output of the primary coil. As a result of this decrease in power output, depletion of the power source is minimized and inadvertent heating of nearby objects can be avoided.

In some embodiments, decreasing the power output of the primary coil reduces the average power output of the primary coil. The average power output of the primary coil can be reduced in a number of ways. For example, in some embodiments the power output duty cycle of the primary coil can be varied in order to reduce the average power output. In other embodiments, the power output can be reduced by a percentage value in order to reduce the average power output of the primary coil.

In embodiments that reduce the average power output of the primary coil by reducing the output by a percentage value, the value can be chosen according to user preference. Preferably, however, the value should be large enough to prevent inadvertent heating of nearby objects when the primary coil is operated away from an implanted secondary coil. In some case, this means the value is high enough to reduce the primary coil output power to zero power, which is intended to encompass substantially no power, e.g., less than 10 percent of maximum power, or more preferably less than 1 percent of maximum power. In some implementations, the value need not reduce the output power to zero power.

The method can utilize any form of response when determining if a response from a secondary coil is detected. In some embodiments, the response from the secondary coil is in the form of one or more detectable feedback indications. These detectable feedback indications can, in some embodiments, be implemented as surges in voltage or current on the power signal between the primary and secondary coils. Such indications can be detected by appropriate detection circuitry connected to the primary coil.

The method can further include the step of waiting a first period of time before determining that no response has been received. This is done to compensate for any delay, temporary interference, or error that might prevent an implanted secondary coil from producing a detectable response. In some cases, this delay may be necessary, such as when an implanted device does not include an implanted charge storage device (or has a depleted one) and the implanted device is therefore dependent on the transmitted power from the primary coil to operate and create the detectable response. This time period can be chosen according to user preference, but should be short enough to prevent inadvertent heating of nearby objects if no secondary coil is present. In some implementations, the first time period is about 2 milliseconds.

In certain embodiments, if a response is detected by the primary coil, the method can include holding or adjusting the power output of the primary coil in response to the requirements of the secondary coil.

If, however, no response is received during the first period of time, the method can include the steps of reducing the power output of the primary coil to zero. Alternatively, the power output can be decreased at a linear rate after the first period of time elapses.

Because a primary coil may be removed from a secondary coil and subsequently re-coupled, it can be desirable to continually probe for the presence of a secondary coil. To this end, in some embodiments, the method can include holding the power output of the primary coil at a decreased level for a second period of time if no response is received during the first period of time, and then repeating the method steps listed above after the second period of time elapses. In this way, the primary coil continually transmits power, determines if a secondary coil is present, and decreases power if no coil is detected.

The second period of time can also be chosen according to user preference. However, the second period of time should be short enough to prevent a user-noticeable delay in transmitting power once the primary coil is re-coupled with a secondary coil. In some embodiments, the second period of time is about 3 seconds.

In another aspect of the invention, an external transcutaneous energy transfer system for use with an implanted medical device is provided including a primary coil configured to transcutaneously transmit energy to the implanted medical device. The system can further include controlling circuitry connected to the primary coil. The controlling circuitry can include a functionality to detect a response from the implanted medical device and the controlling circuitry can be configured to (a) transmit power transcutaneously through the primary coil, (b) determine whether a response from the implanted medical device is detected, and (c) decrease the transmitted power if no response is received.

As mentioned above, in some embodiments, the system can be configured to decrease the transmitted power by reducing an average power output of the primary coil. In some embodiments, reducing the average power output of the primary coil can be accomplished by varying the duty cycle of the primary coil. In other embodiments, the average power output can be reduced by reducing the power output of the primary coil by a percentage value.

In some embodiments, the controlling circuitry can be further configured to wait a first period of time before determining that no response has been received. The first period of time can be, in some embodiments, 100 milliseconds.

If no response is received, the controlling circuitry can be configured to decrease the transmitted power by reducing the transmitted power to zero power. In certain other embodiments, the controlling circuitry can decrease the transmitted power by reducing the transmitted power at a linear rate. Again, the power can be decreased at a linear rate to zero, or to some other non-zero value. As mentioned above, the power should preferably be reduced enough to prevent inadvertent heating of nearby objects.

In some embodiments, the controlling circuitry can be further configured to hold the transmitted power at a decreased level for a second period of time if no response is received during the first period of time. The controlling circuitry can then repeat steps (a)-(c) listed above after the second period of time elapses. This allows the primary coil to continually probe for the presence of a secondary coil without remaining at full power at all times.

While the second period of time can be chosen according to user preference, in some embodiments the second period of time is 3 seconds. As mentioned above, the second period of time should be sufficiently short to prevent a user-noticeable delay in transmitting power if a primary coil is re-coupled with a secondary coil.

In some embodiments, if a response is received, the controlling circuitry can be further configured to hold or adjust the transmitted power in response to the requirements of the implanted medical device.

In a third aspect of the invention, an external transcutaneous energy transfer system for use with an implanted medical device is provided comprising a primary coil configured to transcutaneously transmit energy to the implanted medical device and controlling circuitry connected to the primary coil. The controlling circuitry comprises a functionality to detect a response from the implanted medical device and the controlling circuitry is configured to operate the primary coil at a lower average power level when no response is detected.

In some embodiments, the response from the implanted medical device is in the form of one or more detectable feedback indications. As mentioned above, the controlling circuitry can, in some embodiments, be configured to achieve the lower average power level by varying the duty cycle of the primary coil or by reducing the output of the primary coil by a percentage value.

In addition, in certain embodiments, the controlling circuitry can be configured to periodically repeat a process of transmitting power, detecting a response, and lowering the average power level of the primary coil if no response is detected.

In yet another aspect of the invention, a method of controlling power output from a primary coil in a transcutaneous energy transfer system is provided including the steps of transcutaneously transmitting power from the primary coil and determining whether a response from a secondary coil within a patient is detected. If no response is received, the method can include the step of reducing the average power output of the primary coil. This can be accomplished using any of the methods described above, and the process can be configured to periodically repeat in order to continually probe for the presence of a secondary coil.

BRIEF DESCRIPTION OF THE DRAWINGS

The invention will be more fully understood from the following detailed description taken in conjunction with the accompanying drawings, in which.

DETAILED DESCRIPTION

Figure 1:
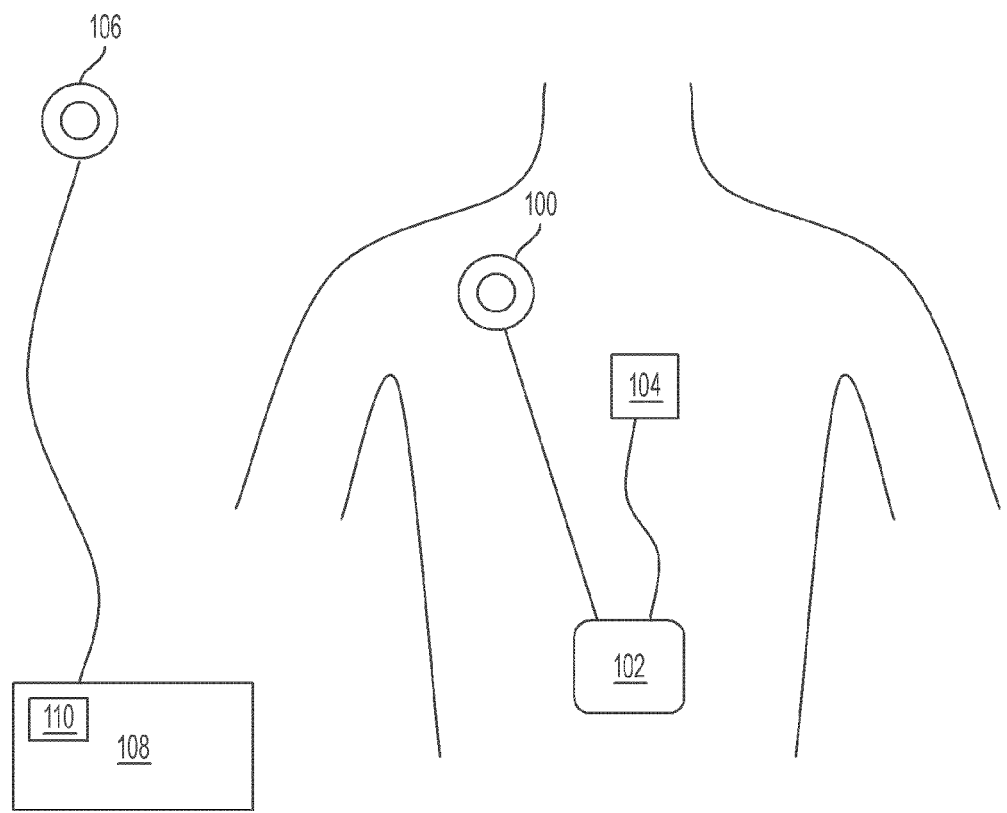
FIG. 1 is an illustration of a exemplary transcutaneous energy transfer (TET) system of the present invention.

Certain exemplary embodiments will now be described to provide an overall understanding of the principles of the methods and systems disclosed herein. One or more examples of these embodiments are illustrated in the accompanying drawings. Those skilled in the art will understand that the methods and systems specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A transcutaneous energy transfer (TET) system works by inductively coupling a primary coil to a secondary coil. The primary coil, configured for disposition outside a patient, is connected to a power source and creates a time-varying magnetic field. When properly aligned with a secondary coil, the time-varying magnetic field from the primary coil induces an alternating electric current in the secondary coil. The secondary coil is configured for implantation inside a patient and can be connected to various other components (e.g., a controller or other management circuitry) that harness the electric current and use it to, for example, charge an implanted battery pack or power an implantable device like a ventricular assist device (VAD), or other cardiac assist device. By utilizing induction to transfer energy, TET systems avoid having to maintain an open passage through a patient's skin to power an implantable device.

As a result of the limited charge storage capacity that can be implanted within the body, patients frequently have to connect the primary coil and external power source to their bodies in order to inductively transfer energy to power an implanted medical device or recharge an implanted battery pack. In some implementations, trained personnel (e.g., doctors, nurses, and other healthcare professionals) connect the primary coil to the patient and configure its operation. In some cases, however, patients connect and disconnect the primary coil on their own.

In either case, it is desirable for the primary coil and external power source to have as simple a user interface as possible in order to prevent user confusion or incorrect configuration of the system. To automate the system, prior art implementations of TET systems utilize a simple "always-on" configuration for the external coil. That is, the primary coil transmits power by creating a time-varying magnetic field so long as it is connected to a power source.

A problem can arise, however, when a patient or trained professional removes the primary coil from the secondary coil without disconnecting the power source. This may be done for any number of reasons, including, for example, to change a patient's clothing, adjust their position, or allow a patient to temporarily travel away from the power source and primary coil. In such a case, the primary coil is often placed on a nearby structure, such as a table. The primary coil, however, is not aware of its altered location and continues to transmit power transcutaneously. The driver will increase the transmitted power hoping to detect a pulse from the secondary coil. The driver behaves this way to correct for changes in alignment, and therefore coupling, in normal use.

This transmission of energy can result in heating of nearby objects, such as metals (e.g., if the primary coil is placed on a ferrous metal table in a hospital). The heating of nearby objects is undesirable because it poses a risk of fire and injury, in addition to being an inefficient use of energy.

To solve this problem, the present invention provides systems and methods of keying the power level output from the primary coil to the presence of a secondary coil in a TET system. In one embodiment, a primary coil can be configured to transmit power transcutaneously and determine whether a response from a secondary coil within a patient is detected. If no response is received within a certain time period, the power output of the primary coil can be decreased to prevent the undesirable waste of energy and the inadvertent heating or excitation of nearby objects. The primary coil can be configured to periodically repeat the process of transmitting power, detecting the presence of a response, and reducing power output in order to continually probe for a secondary coil. If a response from a secondary coil is detected, the primary coil can be configured to continue transmitting power according to the demands of the implanted medical device.

An exemplary TET system adapted for use with the present invention is illustrated in FIG. 1. The system includes an external primary coil 106 that is connected to a power supply 108 and external controlling circuitry 110. Implanted inside a patient is a secondary coil 100 adapted to receive energy transcutaneously from primary coil 106, as well as a controller 102 and a ventricular assist device (VAD) 104, or other implanted assist device.

In use, primary coil 106 can be placed over the area of secondary coil 100 such that they are substantially in axial alignment. The secondary coil 100 can be implanted at various locations in the body, but is often implanted close to the skin to minimize the number of layers of tissue disposed between primary coil 106 and secondary coil 100. Power supply 108, which can include external circuitry 110 for controlling the system to produce a desired output voltage, frequency, and current profile, can be activated to produce a time-varying magnetic field in the primary coil 106. The time-varying magnetic field induces electric current flow in the secondary coil 100. This current can be subsequently distributed to controller 102 and any attached VADs 104 or charge storage devices.

Figure 2:
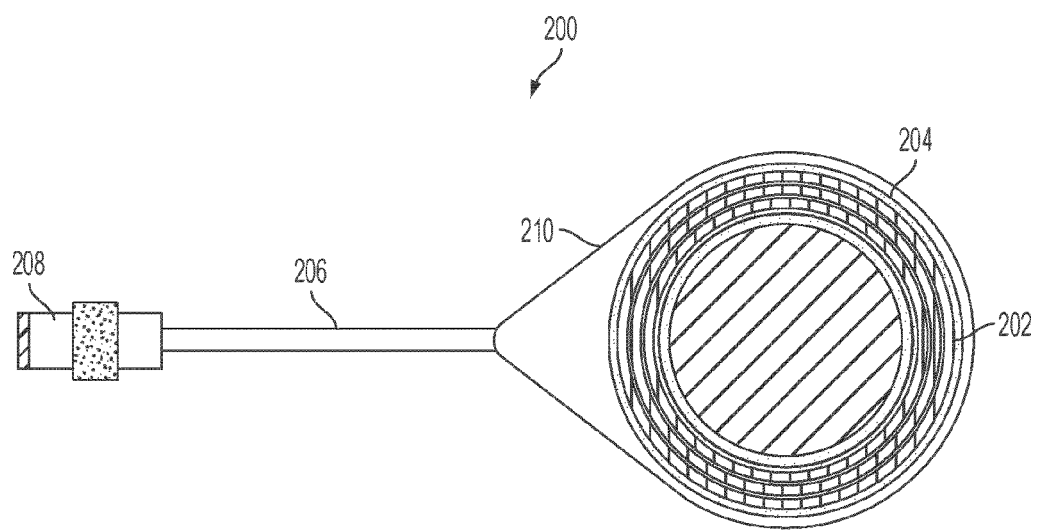
FIG. 2 is an illustration of an exemplary implantable secondary coil of the present invention.

An exemplary secondary coil of the present invention is shown in FIG. 2. Secondary coil 200 features a coil winding portion 202 consisting of several turns of conductive wire, a core 204 containing internal circuitry in connection with the coil portion 202, as well as a connecting portion 206 and an interface portion 208. The coil 200 can be encapsulated in a biocompatible material 210. For example, in an exemplary embodiment, the secondary coil 200 can be encapsulated in epoxy and subsequently dipped in ANGIOFLEX®, polyurethane, or a silicone rubber having low permeability and moisture ingress. These materials can prevent moisture ingress into the secondary coil.

Coil portion 202 can vary in size and turns of wire depending on numerous factors such as the intended implantation site, the desired driving frequency, output power, etc. In an exemplary embodiment, coil portion 202 comprises 13 turns of Litz wire in a two-inch diameter coil. In addition to the wire, the secondary coil 200 can contain a ferrite core 204 that houses internal electronic circuitry which rectifies the alternating current in the coil portion 202 to provide a regulated direct current output voltage to the controller 102 or VAD 104. Coil portion 202 is typically wound around core 204. An exemplary secondary coil using a ferrite core is described in U.S. Patent Pub. No. 2003/0171792, which is hereby incorporated by reference in its entirety.

In some embodiments, the internal circuitry of secondary coil 200 is configured to generate detectable indications that form a feedback loop to the external circuitry 110 and primary coil 106. These detectable indications can be in the form of voltage spikes in the power delivery signal between the primary and secondary coils. An exemplary implementation of feedback indications in a TET system is described in U.S. Pat. No. 6,442,434, entitled "Methods and Apparatus for Providing a Sufficiently Stable Power to a Load in an Energy Transfer System," which is hereby incorporated by reference in its entirety. As described below, these detectable indications can be utilized in systems according to the present invention to determine whether a secondary coil is present.

Secondary coil 200 can also include connecting portion 206 that can be coupled to interface portion 208. Interface portion 208 can be used to connect the secondary coil 200 to a controller 102 or other implanted medical device. The interface portion 208 can include any electrical connector known in the art to facilitate modular connection to a controller 102, or can consist of terminal ends of the wires or other electrical leads that comprise connecting portion 206.

Figure 3:
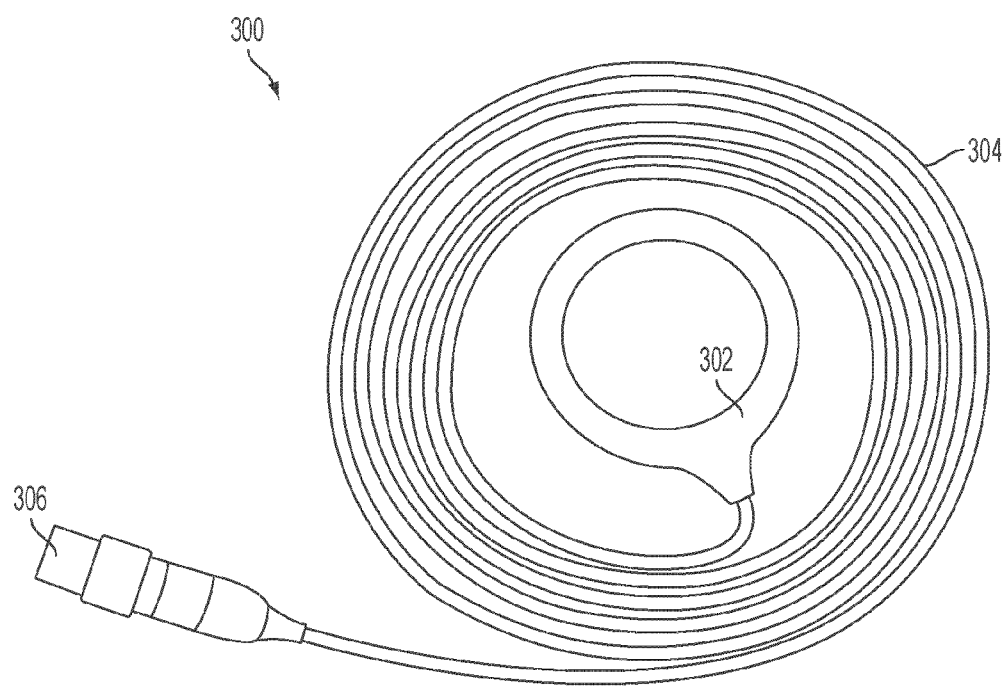
FIG. 3 is an illustration of an exemplary external primary coil of the present invention.

A secondary coil like the one depicted in FIG. 2 can be inductively coupled with, for example, the primary coil 300 illustrated in FIG. 3. Similar to secondary coil 200, primary coil 300 includes a coil portion 302, a connecting portion 304, and an interface portion 306. Primary coil 300 can be adapted to connect, using interface portion 306, to power supply 108 and controlling circuitry 110.

Power supply 108 can include an external battery pack, wall-powered AC adapter, or other power source. Power supply 108 can also include controlling circuitry 110 that implements the TET control system and produces a desired voltage, frequency, and current profile. In some exemplary embodiments, some or all of this circuitry can be included in a separate housing that is connected to both power supply 108 and primary coil 300.

Figure 4:
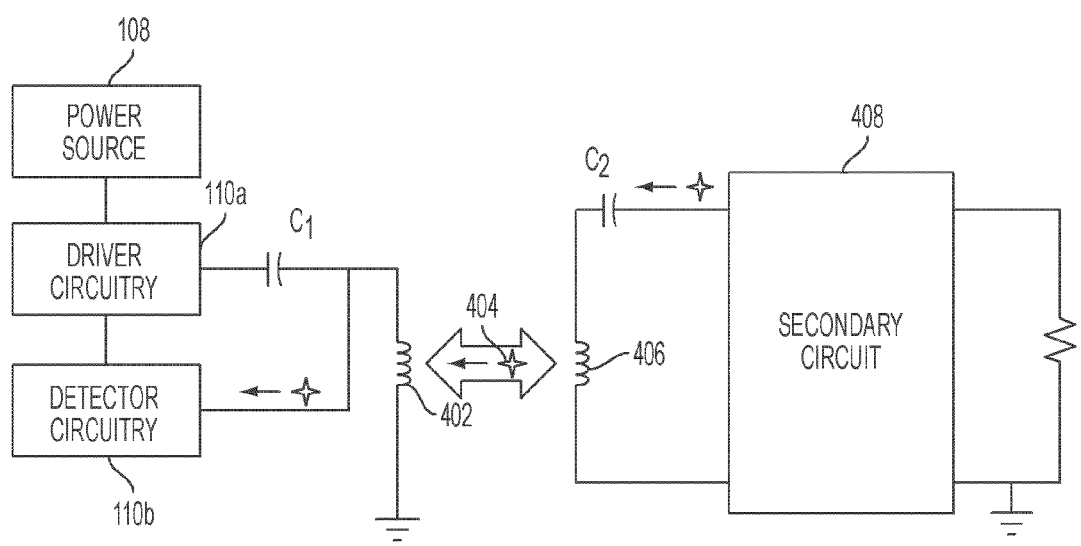
FIG. 4 is a block illustration of an exemplary TET system of the present invention.

FIG. 4 provides a block illustration of an exemplary TET system including an implanted secondary coil, external primary coil, and associated circuitry. Outside of a patient's body is the primary coil 402, which forms a resonant circuit with capacitor $C_1$ that is driven by driver circuitry 110a. Driver circuitry 110a is connected to power source 108 and detector circuitry 110b. U.S. Pat. No. 6,442,434, incorporated by reference above, illustrates an exemplary implementation of driver and detector circuitry 110a, 110b. As described above, all of these circuit components can be combined into a single housing or can be included in separate enclosures that can be connected together.

Implanted inside a patient's body is the secondary coil 406, which also forms a resonant circuit with capacitor $C_2$. Also included can be secondary circuitry 408 that rectifies or otherwise conditions the alternating current received from the secondary coil. U.S. Pat. No. 6,442,434, incorporated by reference above, illustrates an exemplary implementation of secondary circuitry 408. Secondary circuitry 408 can be configured to generate detectable feedback indications 404 that are transmitted from the secondary coil 406 to the primary coil 402 and detected by detector circuitry 110b. The detectable indications 404 can be created, for example, by periodically shorting the resonant circuit of the secondary coil, e.g., by closing a switch across the circuit of capacitor $C_2$ and secondary coil 406, to create a momentary spike in the current running through the circuit. This current spike is reflected in the primary coil and can be detected as a surge in the amplitude of the voltage on the primary coil 402 that is measured by the detector circuitry 110b.

The detector circuitry 110b can use any method known in the art to measure the amplitude of the voltage on the primary coil 402 to determine if a response from the secondary coil is detected. For example, the detector circuitry 110b can comprise a comparator which receives as an input the primary coil amplitude signal and a detectable indication threshold signal that tracks a short-term average of the monitored primary coil amplitude signal. The threshold signal can also include a diode offset to provide some noise immunity (i.e., to help avoid false-positive detection of indications from the secondary coil). The comparator can be configured to output a detection signal when a significant difference between the primary coil amplitude signal and the threshold signal is detected. An Analog/Digital (A/D) converter integrated into a microprocessor can also be used to detect and filter a response from the secondary coil. The driver circuitry 110a, and other components of the controlling circuitry 110, can then respond to the comparator's output signal, or lack thereof, to regulate the power output of the primary coil according to the methods described herein. U.S. Pat. No. 6,442,434, incorporated by reference above, more particularly describes an exemplary implementation of a detector circuit capable of determining if feedback indications are received from a secondary coil.

In exemplary embodiments, each of the secondary coil components are contained within the ferrite core 204 illustrated in FIG. 2. Such a configuration allows the secondary coil 200 to output a rectified DC voltage to the controller 102 or other implanted medical device that can be utilized to, for example, power an implanted VAD or other assist device, or recharge an implanted battery pack.

While the configuration shown in FIG. 4 represents one exemplary embodiment of TET system adapted for use in the present invention, other implementations are also possible. There are a number of ways to create detectable indications on the inductive link, or through other channels, between the primary and secondary coils, all of which are considered to be within the scope of the present invention.

Figure 5:
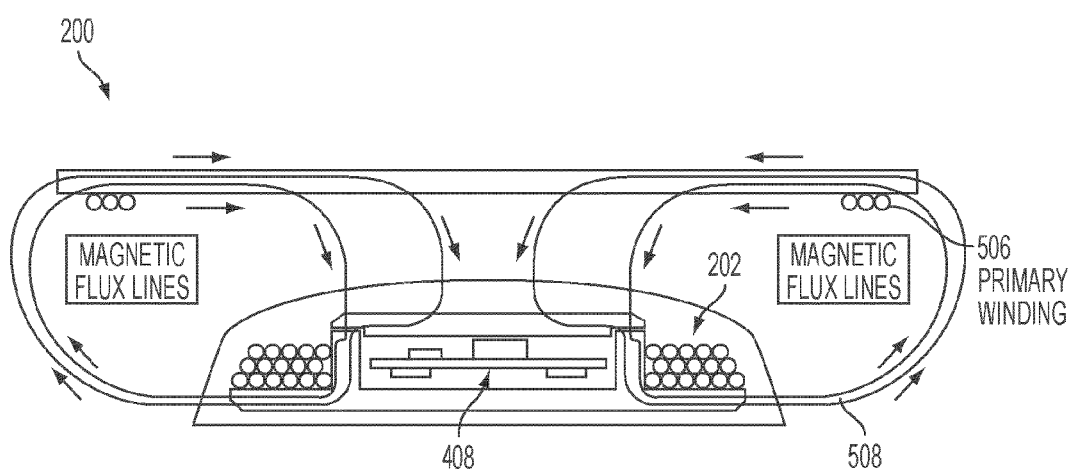
FIG. 5 is an illustration of an exemplary external primary coil in proximity to an exemplary secondary coil that illustrates exemplary lines of magnetic flux.

As mentioned above, the primary coil 106 creates a time-varying magnetic field when powered by power source 108. The magnetic field emitted by the primary coil induces the flow of electric current in secondary coil 100 when the coils are properly aligned. FIG. 5 illustrates such alignment between the two coils. A primary winding 506, similar to the coil portion 302 of primary coil 300, is shown emitting representative lines of magnetic flux 508. The magnetic field (illustrated by the lines of magnetic flux) induces electric current flow in the coil windings 202 of the exemplary secondary coil 200 (shown here in cross section illustrating the secondary circuitry 408 contained within the ferrite core 204).

A similar magnetic field (and similar representative lines of magnetic flux) is created by a powered primary coil even in the absence of a secondary coil. It is this magnetic field that can cause heating in nearby objects when the primary coil is not aligned with a secondary coil.

Figure 6:
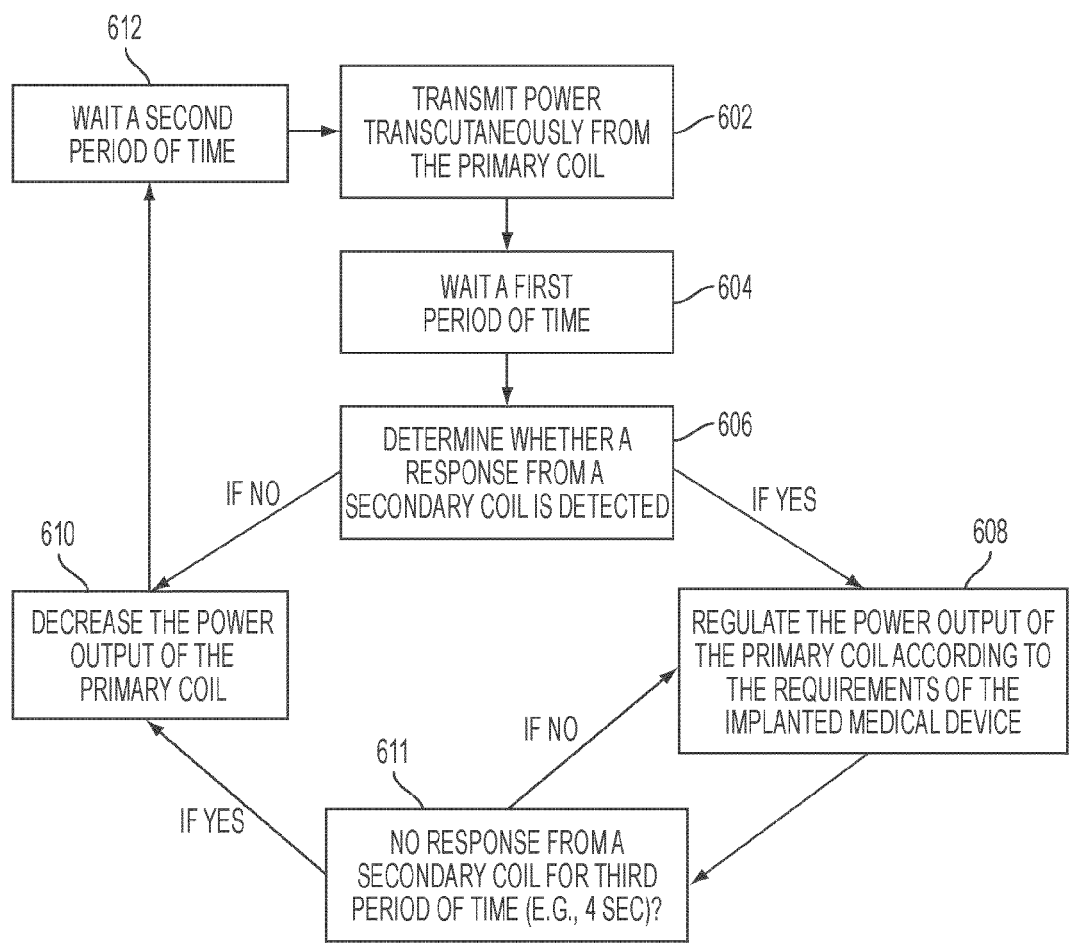
FIG. 6 is a flow diagram illustrating an implementation of the power control method of the present invention.

The present invention addresses this problem by providing a method of controlling power output from a primary coil in a transcutaneous energy transfer system. The method is illustrated in FIG. 6, and includes transmitting power transcutaneously from a primary coil [step 602]. Power is transmitted because, in the case of implanted medical devices having no implanted charge storage devices, the implanted device cannot operate and produce a detectable response until it receives power from the primary coil. In addition, in some embodiments, the detectable response from the secondary coil is in the form of detectable feedback indications created on the power signal between the primary and secondary coils, as described above. In these embodiments, the power delivery signal must first exist before detectable indications can be created on it, e.g., by periodically shorting the resonant circuit of the secondary coil, as described above.

The method further includes determining whether a response from a secondary coil is detected [step 606]. This can be done in a number of ways, including, as described above, by utilizing detector circuitry 110b to detect one or more detectable feedback indications on the power signal between the primary and secondary coils. Detector circuitry 110b can operate, for example, by comparing the measured instantaneous amplitude of the voltage in the primary coil with a threshold signal that tracks the short-term average of the voltage amplitude. When a significant difference between the two signals exists (e.g., as measured by a comparator), a determination can be made that a feedback indication has been detected.

The primary coil 106, or associated controlling circuitry 110, can be configured to wait a first period of time before making the determination regarding whether a response has been received from an implanted secondary coil [step 604]. It should be appreciated that detection of a response can be essentially instantaneous and the waiting period before determining whether coupling between the coils has been achieved can likewise be essentially zero. However, waiting a first period of time of some predetermined duration, e.g., one millisecond, one hundred milliseconds, or more, while transmitting power transcutaneously can be beneficial because it provides tolerance for temporary errors, powering up of the implanted medical device, or temporary interference from external signals. The first period of time should be determined such that only insignificant inadvertent heating would occur in the absence of a secondary coil. In some embodiments, the first period of time is about one hundred milliseconds.

If the primary coil or external circuitry detects a response from an implanted medical device, then the primary coil can continue to safely transmit power transcutaneously. The primary coil can regulate the amount of power transmitted via regulation schemes known in the art [step 608]. One such scheme is described in U.S. Pat. No. 6,442,434, incorporated by reference above.

However, if the primary coil or external circuitry does not detect a response from an implanted medical device within a certain period of time (e.g., a third period of time), it may be that the coil was removed from the patient and, for example, placed on a nearby structure [step 611]. In some embodiments, the third period of time can be, for example, 4 seconds. Accordingly, the power output of the primary coil can be decreased in order to prevent inadvertent heating or excitation of nearby objects [step 610].

The decrease in power can be accomplished in a variety of ways. In some embodiments, the power output of the primary coil can be reduced to zero. In other embodiments, the power output of the primary coil can be reduced at a linear rate to zero, or to some percentage value of the normal operating power, e.g., 20% of the normal operating power.

The decrease in power can also be accomplished by operating the primary coil at a lower average power level than during normal operation (e.g., the level of power output used at step 602). A lower average power level can be achieved by altering the duty cycle of the primary coil, or by reducing the power output of the primary coil by a percentage amount. This may bring the primary coil to a zero power state, which is intended to encompass substantially no power, e.g., less than 10 percent of maximum power, and more preferably less than 1 percent of maximum power. In some embodiments, the primary coil may operate above zero power, but still have an average power level lower than during normal operation.

In order to continually probe for the presence of a secondary coil, the primary coil can be further configured to wait a certain period of time (e.g., a second period of time) while operating at a lower average power level and then repeat the process of transmitting power and determining if a response is detected [step 612]. The second period of time can be set for any interval, but preferably should be short enough to prevent a user-noticeable delay in transmitting power if the primary coil is re-coupled with a secondary coil. In some embodiments, the second period of time is about 3 seconds. In certain embodiments, the second and third periods of time can be equal in length.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A method of controlling power output from a primary coil in a transcutaneous energy transfer system, comprising:
   transcutaneously transmitting power from the primary coil;
   determining whether a response from a secondary coil within a patient is detected; and
   if no response from the secondary coil is detected, decreasing the power output of the primary coil.

2. The method of claim 1, wherein the step of decreasing the power output of the primary coil comprises reducing an average power output of the primary coil.

3. The method of claim 2, wherein the step of reducing the average power output of the primary coil is accomplished by varying a duty cycle of the primary coil.

4. The method of claim 2, wherein the step of reducing the average power output of the primary coil is accomplished by reducing the power output of the primary coil by a percentage value.

5. The method of claim 4, wherein the percentage value is large enough to prevent inadvertent heating of a nearby object.

6. The method of claim 1, wherein the method further comprises waiting a first period of time before determining that the response has not been received.

7. The method of claim 1, wherein the method further comprises holding or adjusting the power output of the primary coil in response to requirements of the secondary coil if the response from the secondary coil is received.

8. The method of claim 6, wherein the first period of time is 100 milliseconds.

9. The method of claim 6, wherein the power output of the primary coil is reduced to zero after the first period of time elapses.

10. The method of claim 6, wherein the power output of the primary coil is decreased at a linear rate after the first period of time elapses.

11. The method of claim 6, further comprising:
holding the power output of the primary coil at a decreased level for a second period of time if the response is not received during the first period of time; and
after the second period of time elapses:
transcutaneously transmitting power from the primary coil;
determining whether the response from the secondary coil is detected; and
if no response is received, decreasing the power output of the primary coil.

12. The method of claim 11, wherein the decreased level of the power output is zero.

13. The method of claim 11, wherein the second period of time is 3 seconds.

14. The method of claim 1, wherein the response from the secondary coil is in a form of one or more detectable feedback indications.

15. A method of controlling power output from a primary coil in a transcutaneous energy transfer system, comprising:
transcutaneously transmitting power from the primary coil;
determining whether a response from a secondary coil within a patient is detected; and
if no response is detected, reducing an average power output of the primary coil while the primary coil and the secondary coil are de-coupled.

16. The method of claim 15, wherein the response from an implanted medical device is in a form of one or more detectable feedback indications.

17. The method of claim 15, wherein the step of reducing the average power output is accomplished by varying a duty cycle of the primary coil.

18. The method of claim 15, wherein the step of reducing the average power output is accomplished by reducing the power output of the primary coil by a percentage value.

19. The method of claim 15, wherein the average power output is reduced to zero power.

20. The method of claim 15, further comprising:
holding the average power output of the primary coil at a decreased level for a period of time, and then,
transcutaneously transmitting power from the primary coil;
determining whether the response from the secondary coil is detected; and
if no response is received, reducing the average power output of the primary coil.

* * * * *